US010874100B2

(12) United States Patent
Vanden Heuvel et al.

(10) Patent No.: US 10,874,100 B2
(45) Date of Patent: Dec. 29, 2020

(54) RESIDUAL DISINFECTANT COMPOSITION

(71) Applicant: Kimberly-Clark Worldwide, Inc., Neenah, WI (US)

(72) Inventors: Amy L. Vanden Heuvel, Neenah, WI (US); Douglas R. Hoffman, Neeneha, WI (US); Jeremy D. Paulsen, Neenah, WI (US); Rebecca Vongsa, Neenah, WI (US); Paige N. Anunson, Neenah, WI (US); Lisa M. Kroll, Neenah, WI (US); Corey T. Cunnington, Neenah, WI (US); David W. Koenig, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 127 days.

(21) Appl. No.: 15/744,091

(22) PCT Filed: Jul. 27, 2015

(86) PCT No.: PCT/US2015/042209
§ 371 (c)(1),
(2) Date: Jan. 12, 2018

(87) PCT Pub. No.: WO2017/019009
PCT Pub. Date: Feb. 2, 2017

(65) Prior Publication Data
US 2018/0199567 A1 Jul. 19, 2018

(51) Int. Cl.
| | |
|---|---|
| A01N 25/10 | (2006.01) |
| A01N 25/34 | (2006.01) |
| A61L 2/18 | (2006.01) |
| C09D 7/61 | (2018.01) |
| C09D 7/63 | (2018.01) |
| A01N 25/04 | (2006.01) |
| A01N 33/12 | (2006.01) |
| A01N 37/36 | (2006.01) |
| A01N 59/26 | (2006.01) |
| C09D 5/14 | (2006.01) |
| A01N 25/30 | (2006.01) |
| A01N 43/36 | (2006.01) |
| C09D 139/06 | (2006.01) |

(52) U.S. Cl.
CPC ............ A01N 25/10 (2013.01); A01N 25/04 (2013.01); A01N 25/34 (2013.01); A01N 33/12 (2013.01); A01N 37/36 (2013.01); A01N 59/26 (2013.01); A61L 2/18 (2013.01); C09D 5/14 (2013.01); C09D 7/61 (2018.01); C09D 7/63 (2018.01); C09D 139/06 (2013.01)

(58) Field of Classification Search
CPC ........ A01N 25/10; A01N 25/34; A01N 25/04; A01N 33/12; A01N 37/36; A01N 59/26; A01N 25/30; A01N 43/36; A61L 2/18; C09D 7/61; C09D 7/63; C09D 5/14; C09D 139/06
See application file for complete search history.

(56) References Cited

U.S. PATENT DOCUMENTS

| | | |
|---|---|---|
| 3,494,821 A | 2/1970 | Evans |
| 3,954,960 A | 5/1976 | Valan |
| 4,100,324 A | 7/1978 | Anderson et al. |
| 4,144,370 A | 3/1979 | Boulton |
| 4,223,009 A | 9/1980 | Chakrabarti |
| 4,445,521 A | 5/1984 | Grollier et al. |
| 4,719,235 A | 1/1988 | Kern |
| 5,057,361 A | 10/1991 | Sayovitz et al. |
| 5,240,764 A | 8/1993 | Haid et al. |
| 5,284,703 A | 2/1994 | Everhart et al. |
| 5,350,624 A | 9/1994 | Georger et al. |
| 5,785,179 A | 7/1998 | Buczwinski et al. |
| 5,964,351 A | 10/1999 | Zander |
| 6,030,331 A | 2/2000 | Zander |
| 6,158,614 A | 12/2000 | Haines et al. |
| 6,269,969 B1 | 8/2001 | Huang et al. |
| 6,269,970 B1 | 8/2001 | Huang et al. |
| 6,273,359 B1 | 8/2001 | Newman et al. |
| 6,315,864 B2 | 11/2001 | Anderson et al. |
| 6,403,113 B1 | 6/2002 | Corzani |
| 6,838,078 B2 | 1/2005 | Wang et al. |
| 6,841,527 B2 | 1/2005 | Mitra et al. |

(Continued)

FOREIGN PATENT DOCUMENTS

| | | |
|---|---|---|
| EP | 0 853 941 A2 | 7/1998 |
| EP | 2098217 | 9/2009 |

(Continued)

OTHER PUBLICATIONS

Information on Copolymer Series INCI Name: VP/Dimethylaminoethyl Methacrylate Copolymer from Ashland, Inc. dated May 27, 2015, 2 pages.

(Continued)

Primary Examiner — Trevor Love
(74) Attorney, Agent, or Firm — Dority & Manning, P.A.

(57) ABSTRACT

A disinfectant composition that is capable of inactivating non-enveloped viruses as well as other microorganisms, such as gram negative and gram positive bacteria, fungi, parasites, enveloped viruses, etc., is provided. Through selective control over the nature of the acid(s) employed and the overall pH level, the present inventors have discovered that the composition can achieve rapid antiviral efficacy, particularly against non-enveloped viruses. Once applied to a surface (e.g., hard surface), the disinfectant composition forms a film that remains capable of providing residual antiviral activity. Notably, the present inventors have discovered that the use of a vinylpyrrolidone copolymer in combination with a polyquaternary ammonium polymer and cationic surfactant can have a synergistic effect on the stability of the film such that it can also achieve long-term, residual antiviral activity.

29 Claims, No Drawings

(56) References Cited

U.S. PATENT DOCUMENTS

| | | |
|---|---|---|
| 7,598,214 B2 | 10/2009 | Cusack et al. |
| 8,034,844 B2 | 10/2011 | Fox et al. |
| 8,105,999 B2 | 1/2012 | Cusack et al. |
| 8,119,115 B2 | 2/2012 | Snyder et al. |
| 8,198,326 B2 | 6/2012 | Scholz |
| 8,337,872 B2 | 12/2012 | Fuls et al. |
| 8,343,523 B2 | 1/2013 | Toreki et al. |
| 8,450,378 B2 | 5/2013 | Snyder et al. |
| 8,512,273 B2 | 8/2013 | Rantala et al. |
| 8,673,835 B2 | 3/2014 | Cusack et al. |
| 9,028,852 B2 | 5/2015 | Scholz |
| 9,232,790 B2 | 1/2016 | Moen et al. |
| 9,321,803 B2 | 4/2016 | Jiang et al. |
| 9,629,361 B2 | 4/2017 | Macinga et al. |
| 9,826,770 B2 | 11/2017 | Scholz et al. |
| 2004/0228809 A1 | 11/2004 | Birkel et al. |
| 2004/0241130 A1 | 12/2004 | Tamareselvy et al. |
| 2007/0166344 A1 | 7/2007 | Qu et al. |
| 2008/0045491 A1 | 2/2008 | Fitchmun |
| 2008/0145390 A1 | 6/2008 | Taylor et al. |
| 2008/0199535 A1 | 8/2008 | Taylor et al. |
| 2008/0317795 A1* | 12/2008 | Traynor .......... A61K 8/062 424/401 |
| 2010/0254924 A1* | 10/2010 | Hamilton .......... A61K 8/342 424/62 |
| 2010/0255121 A1 | 10/2010 | Perry |
| 2010/0316586 A1* | 12/2010 | Knappe .......... A61K 8/8147 424/70.16 |
| 2012/0171155 A1 | 7/2012 | Cunningham et al. |
| 2012/0171267 A1 | 7/2012 | Cunningham et al. |
| 2012/0171300 A1 | 7/2012 | Koenig et al. |
| 2012/0171301 A1 | 7/2012 | Koenig et al. |
| 2014/0369953 A1 | 12/2014 | Purschwitz et al. |

FOREIGN PATENT DOCUMENTS

| | | |
|---|---|---|
| EP | 1 531 671 B1 | 10/2013 |
| EP | 2 774 481 A1 | 9/2014 |
| EP | 2 807 925 A1 | 12/2014 |
| GB | 1 331 819 | 9/1973 |
| WO | WO 00/27271 A2 | 5/2000 |
| WO | WO 01/28337 A2 | 4/2001 |
| WO | WO 01/29315 A1 | 4/2001 |
| WO | WO 2006/062845 A2 | 6/2006 |
| WO | WO 2006/062857 A2 | 6/2006 |
| WO | WO 2012/084863 A1 | 6/2012 |
| WO | WO 2014/158761 A1 | 10/2014 |
| WO | WO2015072125 | 5/2015 |
| WO | WO 2017/019010 A1 | 2/2017 |

OTHER PUBLICATIONS

Search Report and Written Opinion for PCT/US2015/042209 dated Dec. 21, 2015, 19 pages.
European Search Report for PCT/US2015/052209 dated Jan. 2, 2019, 8 pages.
European Search Report for 20176595.5 dated Jul. 10, 2020.

* cited by examiner

RESIDUAL DISINFECTANT COMPOSITION

CROSS REFERENCE TO RELATED APPLICATIONS

This application is the national stage entry of International Patent Application No. PCT/US2015/042209 having a filing date of Jul. 27, 2015, which is incorporated herein in its entirety by reference thereto.

BACKGROUND OF THE INVENTION

Pathogenic viruses are generally classified into two general types: enveloped and non-enveloped viruses. Some well-known enveloped viruses include herpes virus, influenza virus; paramyxovirus, respiratory syncytial virus, coronavirus, HIV, hepatitis B virus, hepatitis C virus, SARS-CoV, and togavirus. Non-enveloped viruses, sometimes referred to as "naked" viruses, include the families Picornaviridae, Reoviridae, Caliciviridae, Adenoviridae, Papovaviridae, and Parvoviridae. Members of these families include rhinovirus, poliovirus, adenovirus, hepatitis A virus, norovirus, papillomavirus, enterovirus, coxsackievirus, and rotavirus. "Enveloped" viruses are relatively sensitive and, thus, can be inactivated by commonly used disinfectants. In contrast, "non-enveloped" viruses are substantially more resistant to conventional disinfectants and are more environmentally stable than enveloped viruses. Thus, most disinfectants have insufficient efficacy against these types of non-enveloped viruses. Another problem with many conventional disinfectants is that they can kill microorganisms on surfaces when applied and allowed to remain in contact for a specific time, such as 10 minutes. However, the disinfectant does not typically persist on the surface. Normal stresses to the surface, like rinsing, repeated touching or wiping with a cloth, tend to physically remove any residual disinfectant ingredients from the surface. Thus, if the surface becomes re-contaminated again, the disinfectant must be re-applied to kill the newly deposited organisms.

As such, a need currently exists for a disinfectant composition that is capable of exhibiting antiviral efficacy immediately upon contact with a virus and after an extended period of time on a surface.

SUMMARY OF THE INVENTION

In accordance with one embodiment of the present invention, a disinfectant composition is disclosed that comprises:
i) an acid;
ii) a vinylpyrrolidone copolymer having the following general formula:

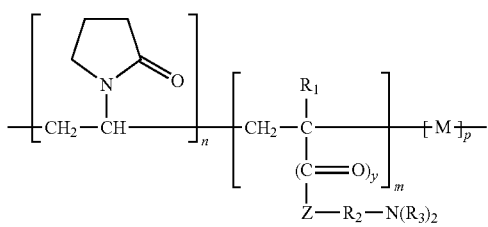

wherein,
n is from 20 to 99;
m is from 1 to 80;
p is from 0 to 50, and wherein the total of n+m+p is 100;
$R_1$ is H or a $C_1$ to $C_4$ alkyl;
Z is O, S, or NH;
$R_2$ is $(CH_2)_x$;
x is from 1 to 18;
y is 0 or 1;
$R_3$ is independently hydrogen or a $C_1$ to $C_4$ alkyl; and
M is a vinyl or vinylidene monomer copolymerizable with vinyl pyrrolidone;
iii) a polyquaternary ammonium polymer having the following general structure:

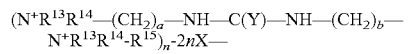

wherein,
$R^{13}$ and $R^{14}$ are independently alkyl, hydroxyalkyl, or $-CH_2CH_2(OCH_2CH_2)_cOH$;
$R^{15}$ is a linking group and may be $(CH_2)_d$ or $\{(CH_2)_eO(CH_2)_f\}_g$;
Y is O, S or NH;
a, b, c, d, e and f are each independently from 1 to 6;
g is from 1 to 4;
n is at least 2; and
$X^-$ is an anion; and
iv) a cationic surfactant.

The composition has a pH of about 4.5 or less. The vinylpyrrolidone copolymer is present in an amount from about 50 to about 90 parts per 100 parts of acids employed in the composition, and the polyquaternary ammonium polymer is present in an amount from about 30 to about 70 parts per 100 parts of acids employed in the composition.

In accordance with another embodiment of the present invention, a film is disclosed that is capable of exhibiting residual antiviral activity. The film comprises an acid, a vinylpyrrolidone copolymer, and a polyquaternary ammonium polymer, such as described above. The vinylpyrrolidone copolymer is present in an amount from about 50 to about 90 parts per 100 parts of acids employed in the composition, and the polyquaternary ammonium polymer is present in an amount from about 30 to about 70 parts per 100 parts of acids employed in the composition.

Other features and aspects of the present invention are discussed in greater detail below.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a disinfectant composition that is capable of inactivating non-enveloped viruses as well as other microorganisms, such as gram negative and gram positive bacteria, fungi, parasites, enveloped viruses, etc. In one embodiment, the composition is effective against non-enveloped viruses, including members of the families Picornaviridae, Reoviridae, Caliciviridae, Adenoviridae, Papovaviridae, and Parvoviridae, which includes non-enveloped viruses such as rhinovirus, poliovirus, enterovirus, coxsackievirus, adenovirus, norovirus, papillomavirus, feline calicivirus, hepatitis A virus, parvovirus, and rotavirus. The disinfectant composition contains at least one acid and has a pH of about 4.5 or less, in some embodiments about 4.0 or less, and in some embodiments, from about 1.0 to about 3.5. Through selective control over the nature of the acid(s) employed and the overall pH level, the present inventors have discovered that the composition can achieve rapid antiviral efficacy, particularly against non-enveloped viruses. For example, after being exposed to a virus for 10 minutes, the disinfectant composition can exhibit a $\log_{10}$ reduction of about 1.5 or more, in some embodiments about 2.0 or more, in some embodiments about 2.5 or more, and in some embodiments, from about 3.0 to about 5.0, such as determined in accordance with ASTM E1052-11. In one embodiment, for instance, the disinfectant composition may exhibit a $\log_{10}$ reduction after 10 minutes within the ranges noted above against a feline calicivirus. In another embodiment, the disinfectant composition may exhibit a $\log_{10}$ reduction after 10 minutes within the ranges noted above against Phi X174 (ATCC 13706-B1), a non-enveloped bacteriophage employed as a surrogate for non-enveloped viruses (e.g., norovirus).

Once applied to a surface (e.g., hard surface), the disinfectant composition forms a film that remains capable of providing residual antiviral activity. For example, after being exposed to a virus for 10 minutes, the film itself can exhibit a $\log_{10}$ reduction of about 0.5 or more, in some embodiments about 0.8 or more, in some embodiments about 1.0 or more, and in some embodiments, from about 1.2 to about 3.0. Notably, the present inventors have discovered that the use of a vinylpyrrolidone copolymer in combination with a polyquaternary ammonium polymer and cationic surfactant can have a synergistic effect on the stability of the film such that it can also achieve long-term, residual antiviral activity. For example, the film can exhibit antiviral activity after a substantial period of time on the surface, such as after 24 hours, and in some cases, even after 48 hours. In one embodiment, for instance, the film may exhibit a $\log_{10}$ reduction after 24 or 48 hours within the ranges noted above against a feline calicivirus. In another embodiment, the film may exhibit a $\log_{10}$ reduction after 24 hours or 48 hours within the ranges noted above against Phi-X 174 (ATCC 13706-B1).

Various embodiments of the present invention will now be described in more detail below.

I. Disinfectant Composition

A. Acids

Acids are typically employed in the disinfectant composition in an amount of from about 0.1 wt. % to about 10 wt. %, in some embodiments from about 0.5 to about 8 wt. %, and in some embodiments, from about 0.8 wt. % to about 1.5 wt. % of the composition.

Any of a variety of acids may generally be employed, such as inorganic acids (e.g., phosphoric acid, boric acid, hydrobromic acid, molybdic acid, etc.), organic acids, and so forth. Particularly suitable organic acids are carboxylic acids having the following general formula, R—COOH, wherein, "R" is an optionally substituted alkyl, optionally substituted alkenyl, optionally substituted aryl (e.g., phenyl), and so forth. In certain cases, "R" may be an optionally substituted lower alkyl having only from 1 to 6 carbon atoms. The term "substituted" indicates that one or more atoms are substituted by functional groups, such as halogen atoms (F, Cl, Br, I), hydroxyl groups, amino groups, thiol groups, nitro groups, cyano groups, etc. Some examples of suitable organic carboxylic acids for use in the composition of the present invention may include, for instance, citric acid, malic acid, maleic acid, mandelic acid, succinic acid, sulfosuccinic acid, tannic acid, lactic acid, glyoxylic acid, gallic acid, fumaric acid, tartaric acid, formic acid, benzoic acid, 4-aminobenzoic acid, 4-bromo-DL-mandelic acid, etc. Regardless of whether inorganic or organic acids are employed, acids having a relatively low first acid dissociation constant ($pK_{a1}$) have been found to be particularly suitable for use in the present invention. For example, the acid may have a $pk_{a1}$ value of from about 5.0 or less, in some embodiments about 4.0 or less, and in some embodiments, from about 1.0 to about 3.5, as determined at a temperature of 25° C. Specific examples of such acids include, for instance, maleic acid ($pk_{a1}$ of 1.9), phosphoric acid ($pk_{a1}$ of 2.18), glyoxylic acid ($pk_a$ of 3.18), and so forth.

B. Vinylpyrrolidone Copolymer

The vinylpyrrolidone copolymer employed in the disinfectant composition of the present invention generally has the following formula:

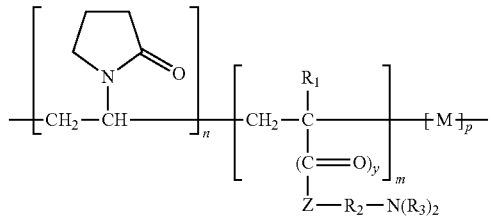

wherein, n is from 20 to 99, and in some embodiments, from 40 to 90, m is from 1 to 80, and in some embodiments, from 5 to 40;

p is from 0 to 50, and in some embodiments, from 5 to 20, and wherein the total of n+m+p is typically 100;

$R_1$ is H or a $C_1$ to $C_4$ alkyl (e.g., $CH_3$);

Z is O, S, or NH, and in some embodiments, O;

$R_2$ is $(CH_2)_x$;

x is from 1 to 18, and in some embodiments, from 2 to 10;

y is 0 or 1;

$R_3$ is independently hydrogen or a $C_1$ to $C_4$ alkyl (e.g., $CH_3$); and

M is a vinyl or vinylidene monomer copolymerizable with vinyl pyrrolidone.

The monomer unit [ ]$_m$ is, for example, a di-lower alkylamine alkyl (meth)acrylate or a vinyl ether derivative. Examples of these monomers include, for instance, dimethylaminomethyl acrylate, dimethylaminomethyl methacrylate, diethylaminomethyl acrylate, diethylaminomethyl methacrylate, dimethylaminoethyl acrylate, dimethylaminoethyl methacrylate, dimethylaminobutyl acrylate, dimethylaminobutyl methacrylate, dimethylaminoamyl methacrylate, diethylaminoamyl methacrylate, dimethylaminohexyl acrylate, diethylaminohexyl methacrylate, dimethylaminooctyl acrylate, dimethylaminooctyl methacrylate, diethylaminooctyl acrylate, diethylaminooctyl methacrylate, dimethylaminodecyl methacrylate, dimethylaminododecyl methacrylate, diethylaminolauryl acrylate, diethylaminolauryl methacrylate, dimethylaminostearyl acrylate, dimethylaminostearyl methacrylate, diethylaminostearyl acrylate, diethylaminostearyl methacrylate, di-t-butylaminoethyl methacrylate, di-t-butylaminoethyl acrylate, dimethylamino vinyl ether, etc., as well as combinations thereof.

The monomer unit "M", which is optional, may include any conventional vinyl monomer copolymerizable with N-vinyl pyrrolidone. Thus, for example, suitable conventional vinyl monomers include alkyl vinyl ethers (e.g., methyl vinyl ether, ethyl vinyl ether, octyl vinyl ether, etc.); acrylic and methacrylic acid and esters thereof (e.g., methacrylate, methyl methacrylate, etc.); vinyl aromatic monomers (e.g., styrene, α-methyl styrene, etc.); vinyl acetate; vinyl alcohol; vinylidene chloride; acrylonitrile and substituted derivatives thereof; methacrylonitrile and substituted derivatives thereof; acrylamide and methacrylamide and N-substituted derivatives thereof; vinyl chloride, crotonic acid and esters thereof; etc.

In certain embodiments, $R_1$ and/or $R_3$ may be methyl. Likewise, y may be 1 and/or $R_2$ may be $(CH_2)_2$ or $(CH_2)_3$. One particular example of such a polymer is a vinylpyrrolidone/dimethyl-aminoethylmethacrylate copolymer, which has the following general structure:

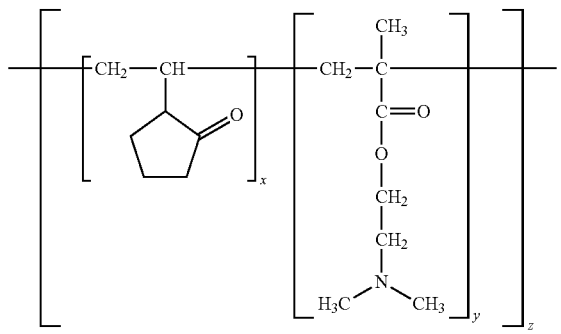

wherein x, y and z are at least 1 and have values selected such that the weight average molecular weight of the vinylpyrrolidone/dimethylamino ethylmethacrylate copolymer is from about 10,000 to about 5,000,000. Commercially available polymers of this type include Copolymer 845, Copolymer 937, and Copolymer 958 (Ashland, Inc.). In yet another embodiment, the vinylpyrrolidone copolymer may have the following general structure:

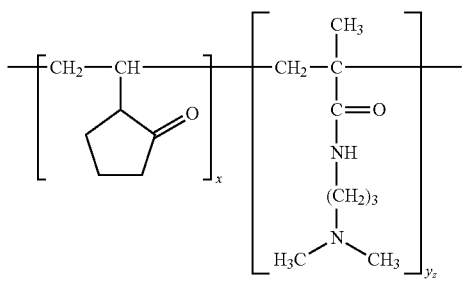

wherein x, y and z are at least 1 and have values selected such that the weight average molecular weight of the copolymer is from about 10,000 to about 5,000,000. Techniques for synthesizing such polymers are well known in the art and described in more detail U.S. Pat. Nos. 4,445,521; 4,223,009; and 3,954,960, as well as GB 1331819.

C. Polyquaternary Ammonium Polymer

As indicated above, a polyquaternary ammonium polymer is also employed in the disinfectant composition that contains two or more quaternary ammonium centers within the compound structure. For instance, the polyquaternary ammonium polymer typically has the following general structure:

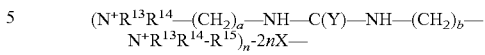

wherein, $R^{13}$ and $R^{14}$ are independently alkyl (e.g., methyl, ethyl, isopropyl, etc.), hydroxyalkyl (e.g., hydroxymethyl, hydroxyethyl, etc.), or $-CH_2CH_2(OCH_2CH_2)_cOH$;

$R^{15}$ is a linking group and may be $(CH_2)_d$ or $\{(CH_2)_eO(CH_2)_f\}_g$;

Y is O, S or NH, and in some embodiments, O;

a, b, c, d, e and f are each independently from 1 to 6, in some embodiments from 1 to 4, and in some embodiments, from 2 to 3;

g is from 1 to 4, and in some embodiments, from 1 to 2;

n is at least 2, in some embodiments from 2 to 200, and in some embodiments, from 3 to 100; and $X^-$ is an anion, such as a halide (e.g., fluoride, chloride, bromide, iodide, and most desirably, chloride), carboxylate, carbonate, bicarbonate, sulfate (e.g., methosulfate, ethosulfate, etc.), and so forth.

In certain embodiments, $R^{13}$ and/or $R^{14}$ may be methyl. Likewise, "a" may be 3 and/or "b" may be 3. $R^{15}$ may likewise be $\{(CH_2)_eO(CH_2)_f\}_g$ and "e" may be 2, "f" may be 2, and/or "g" may be 1. In one particular embodiment, for instance, the polyquaternary ammonium polymer may be poly[bis(2-chloroethyl)ether-alt-1,3-bis[3-(dimethylamino) propyl]urea] quaternized (also known as "Polyquaternium-2" using INCI nomenclature), which has the following general structure:

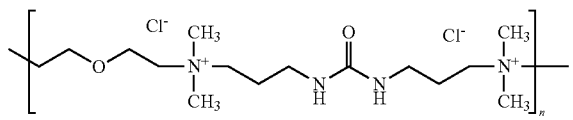

wherein n is as defined above.

The present inventors have discovered that selective control over the relative amount of the vinylpyrrolidone copolymer and polyquaternary ammonium polymer in relation to acids within the composition can have a significant impact on residual efficacy. For example, vinylpyrrolidone copolymers may be present in an amount of from about 50 to about 90 parts, in some embodiments from about 60 to about 90 parts, and in some embodiments, from about 65 to about 85 parts per 100 parts of acids employed in the composition. In certain embodiments, for instance, such copolymers may constitute from about 0.2 wt. % to about 5 wt. %, in some embodiments from about 0.5 to about 3 wt. %, and in some embodiments, from about 0.6 to about 2 wt. % of the composition. Likewise, polyquaternary ammonium copolymers may be present in an amount of from about 30 to about 70 parts, in some embodiments from about 35 to about 65 parts, and in some embodiments, from about 40 to about 60 parts per 100 parts of acids employed in the composition. In certain embodiments, for instance, such polymers may constitute from about 0.1 wt. % to about 3 wt. %, in some embodiments from about 0.2 wt. % to about 2 wt. %, and in some embodiments, from about 0.3 to about 1.5 wt. % of the composition. Vinylpyrrolidone copolymers are also typically employed in an amount greater than the polyquaternary ammonium polymers, and the weight ratio of vinylpyrrolidone copolymers to polyquaternary ammonium polymers may be from about 1.0 to about 8.0, in some embodiments from about 1.1 to about 5.0, and in some embodiments, from about 1.2 to about 3.0.

D. Solvent System

A solvent system containing one or more solvents is also typically employed in the disinfectant composition. The solvent system may, for instance, constitute from about 70 wt. % to about 99.9 wt. %, in some embodiments from about 80 wt. % to about 99.6 wt. %, and in some embodiments, from about 90 wt. % to about 99.5 wt. % of the composition. Suitable solvents may include, for instance, water, glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); alcohols (e.g., methanol, ethanol, n-propanol, isopropanol, and butanol); ketones (e.g., acetone, methyl ethyl ketone, and methyl isobutyl ketone); esters (e.g., ethyl acetate, butyl acetate, diethylene glycol ether acetate, methoxypropyl acetate, ethylene carbonate, propylene carbonate, etc.); amides (e.g., dimethylformamide, dimethylacetamide, dimethylcaprylic/capric fatty acid amide and N-alkylpyrrolidones); sulfoxides or sulfones (e.g., dimethyl sulfoxide (DMSO) and sulfolane); and so forth.

While a wide variety of solvents may be employed, one beneficial aspect of the present invention is that can exhibit good antiviral efficacy without the need for alcohol-based solvents (e.g., ethanol) often employed in conventional disinfectant compositions. In fact, the disinfectant composition of the present invention may be generally free of such alcohol-based solvents (e.g., ethanol). When employed, for instance, alcohol-based solvents typically constitute no more than about 5 wt. %, in some embodiments no more than about 3 wt. %, and in some embodiments, from 0 wt. % to about 1 wt. % of the disinfectant composition. Furthermore, water is typically the primary solvent such that the composition is considered "aqueous." In most embodiments, for example, water constitutes at least about 50 wt. %, in some embodiments at least about 75 wt. %, and in some embodiments, from about 90 wt. % to 100 wt. % of the solvent system.

E. Cationic Surfactant

The disinfectant composition also contains one or more cationic surfactants to further enhance the residual antimicrobial activity. When employed, such cationic surfactants may constitute from about 0.1 wt. % to about 15 wt. %, in some embodiments from about 0.2 to about 10 wt. %, and in some embodiments, from about 0.5 to about 5 wt. % of the composition. Examples of suitable cationic surfactants may include, for instance, biguanides and bisbiguanides (e.g., chlorhexidine, polyhexamethylenebiguanide, etc.), quaternary ammonium salts (e.g., benzalkonium chloride and alkyl substituted derivatives, cetylpyridinium halides, benzethonium chloride, etc. Quaternary ammonium salts, for instance, may be particularly useful in the disinfectant composition of the present invention. Such salts typically contain one quaternary ammonium group attached to at least one $C_6$-$C_{18}$ linear or branched alkyl or arylalkyl chain. Particularly suitable compounds of this class may be represented by the following formula:

$R^{21}R^{22}N^+R^{23}R^{24}X^-$ wherein, $R^{21}$ and $R^{22}$ are $C_1$-$C_{18}$ linear or branched alkyl, alkenyl, or arylalkyl chains that may be substituted in available positions by N, O, or S, provided at least one $R^{21}$ or $R^{22}$ is a $C_8$-$C_{18}$ linear or branched alkyl, alkenyl, or arylalkyl chains that may be substituted in available positions by N, O, or S;

$R^{23}$ and $R^{24}$ are $C_1$-$C_6$ alkyl, phenyl, benzyl, or $C_8$-$C_{12}$ arylalkyl groups, or $R^{23}$ and $R^{24}$ may also form a ring (e.g., pyridine ring) with the nitrogen of the quaternary ammonium group; and $X^-$ is an anion, such as a halide (e.g., fluoride, chloride, bromide, iodide, and most desirably, chloride), carboxylate, carbonate, bicarbonate, sulfate (e.g., methosulfate, ethosulfate, etc.), and so forth.

Examples of such compounds include, benzalkonium halides having an alkyl chain length of $C_{12}$-$C_{16}$, benzalkonium halides substituted with alkyl groups on the phenyl ring, dimethyldialkylammonium halides in which the alkyl groups have chain lengths of $C_8$-$C_{18}$, benzethonium halides and alkyl substituted benzethonium halides, and so forth.

F. Other Components

In addition to those noted above, a variety of other components may also be incorporated into the disinfectant composition of the present invention, such as chelators, nonionic surfactants, anionic surfactants, zwitterionic surfactants, propellants, pH adjustors (e.g., sodium hydroxide), fragrances, colorants, preservatives, chaotropic agents, antioxidants, light stabilizers, etc. In one embodiment, for instance, one or more nonionic surfactants may be employed, such as in an amount from about 0.1 wt. % to about 15 wt. %, in some embodiments from about 0.2 to about 10 wt. %, and in some embodiments, from about 0.5 to about 5 wt. % of the composition. Nonionic surfactants typically have a hydrophobic base (e.g., long chain alkyl group or an alkylated aryl group) and a hydrophilic chain (e.g., chain containing ethoxy and/or propoxy moieties). Some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. Particularly suitable nonionic emulsifiers may include ethylene oxide condensates of fatty alcohols (e.g., sold under the trade name Lubrol), polyoxyethylene ethers of fatty acids (particularly $C_{12}$-$C_{20}$ fatty acids), polyoxyethylene sorbitan fatty acid esters (e.g., sold under the trade name TWEEN®), and sorbitan fatty acid esters (e.g., sold under the trade name SPAN™ or ARLACEL®), etc. The fatty components used to form such emulsifiers may be saturated or unsaturated, substituted or unsubstituted, and may contain from 6 to 22 carbon atoms, in some embodiments from 8 to 18 carbon atoms, and in some embodiments, from 12 to 14 carbon atoms.

To help maintain the desired charge, the disinfectant composition of the present invention is generally free of ionic surfactants that are not cationic in nature (i.e., anionic or zwitterionic surfactants). Nevertheless, such surfactants can be employed in certain embodiments, although typically in an amount of no more than about 2 wt. %, in some embodiments no more than about 1 wt. %, and in some embodiments, from 0 wt. % to about 0.5 wt. % of the disinfectant composition.

The composition may also contain a preservative or preservative system to inhibit the growth of microorganisms. Suitable preservatives may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. Other suitable preservatives include those sold by Ashland, Inc., such as "Germall 115" (amidazolidinyl urea), "Germall II" (diazolidinyl urea), and "Germall Plus" (diazolidinyl urea and iodopropynyl butylcarbonate). Another suitable preservative is Kathon CG®, which is a mixture of methylchloroisothiazolinone and methylisothiazolinone available from Dow Chemical; Mackstat H 66 (available from Solvay). Still another suitable preservative system is a combination of 56% propylene glycol, 30% diazolidinyl urea, 11% methylparaben, and 3% propylparaben available under the name GERMABEN® II from Ashland, Inc.

As noted above, the pH of the disinfectant composition is typically controlled so that it is about 4.5 or less, in some embodiments about 4.0 or less, and in some embodiments, from about 1.0 to about 3.5. To help achieve the desired pH level, various pH modifiers may be optionally employed. Some examples of pH modifiers that may be used in the present invention include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine. When utilized, the pH modifier may be present in any effective amount needed to achieve the desired pH level.

II. Use of the Composition

The disinfectant composition may generally be used to reduce microbial or viral populations on a wide variety of surfaces, such as a hard surface or a surface on a user/patient (e.g., skin). Exemplary hard surfaces include, for instance, lavatory fixtures, lavatory appliances (toilets, bidets, shower stalls, bathtubs, sinks, and bathing appliances), walls, flooring surfaces, surfaces associated with food preparation (e.g., tables, counters, restaurant, kitchens, sinks, etc.), surfaces associated with hospital environments, medical laboratories and medical treatment environments. The manner in which the disinfectant composition is applied to a surface can vary as desired. For example, in certain embodiments, the composition may be applied directly to the surface. In such an application, a user generally applies the composition (e.g., with a pump) and then removes the composition from the treated area after a certain period of time using a wipe. In other embodiments, however, it may be desired that the composition is first applied to a wipe prior to use. The wipe may provide an increased surface area to facilitate contact of the composition with microorganisms. In addition, the wipe may also serve other purposes, such as providing water absorption, barrier properties, etc. The wipe may also eliminate microorganisms through frictional forces imparted to the surface.

The wipe may be formed from any of a variety of materials as is well known in the art. Typically, however, the wipe includes a fibrous web that contains absorbent fibers. For example, the wipe may be a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter ("gsm"), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Hardwood fibers, such as *eucalyptus*, maple, birch, aspen, and so forth, can also be used. In certain instances, *eucalyptus* fibers may be particularly desired to increase the softness of the web. *Eucalyptus* fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, bamboo, algae, and so forth. In addition, in some instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; polyhydroxyalkanoate; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al. The relative percentages of such fibers may vary over a wide range depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al. Alternatively, the nonwoven composite may be formed be formed by hydraulically entangling staple length fibers and/or filaments with high-pressure jet streams of water. Various techniques for hydraulically entangling fibers are generally are disclosed, for example, in U.S. Pat. No. 3,494,821 to Evans and U.S. Pat. No. 4,144,370 to Bouolton. Hydraulically entangled nonwoven composites of continuous filaments (e.g., spunbond web) and natural fibers (e.g., pulp) are disclosed, for example, in U.S. Pat. No. 5,284,703 to Everhart, et al. and U.S. Pat. No. 6,315,864 to Anderson, et al. Hydraulically entangled nonwoven composites of staple fiber blends (e.g., polyester and rayon) and natural fibers (e.g., pulp), also known as "spunlaced" fabrics, are described, for example, in U.S. Pat. No. 5,240,764 to Haid, et al.

Regardless of the materials or processes utilized to form the wipe, the basis weight of the wipe is typically from about 20 to about 200 grams per square meter ("gsm"), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al.

The composition may be incorporated into the wipe during its formation or simply coated onto all or a portion of a surface of the wipe using known techniques, such as printing, dipping, spraying, melt extruding, coating (e.g., solvent coating, powder coating, brush coating, etc.), foaming, and so forth. In one embodiment, for example, the composition is applied to the wipe by dipping, spraying, or printing. If desired, the composition may be applied in a pattern that covers from about 5% to about 95%, in some embodiments from about 10% to about 90%, and in some embodiments, from about 20% to about 75% of a surface of the wipe. Such patterned application may have various benefits, including enhanced aesthetic appeal, improved absorbency, etc. The particular type or style of the pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. It should be appreciated that the "pattern" may take on virtually any desired appearance.

If desired, the disinfectant composition may be present on the wipe in the form of a liquid such that the wipe is considered a "wet wipe." The total amount of the disinfectant composition employed in such "wet wipes" (including any solvents) depends in part upon the type of wipe material utilized, the type of container used to store the wipes, the nature of the composition, and the desired end use of the wipes. Generally, however, each wet wipe contains from about 150 wt. % to about 600 wt. %, and desirably from about 300 wt. % to about 500 wt. % of the disinfectant composition on the dry weight of the wipe.

Once applied to a surface (e.g., hard surface), solvents can evaporate from the disinfectant composition so that a film is formed. The solvent content (e.g., water content) of the resulting film may be, for instance, less than about 5 wt. %, in some embodiments less than about 2 wt. %, and in some embodiments, less about 1 wt. %. In such embodiments, the film typically contains acids in an amount of from about 10 wt. % to about 50 wt. %, in some embodiments from about 15 wt. % to about 45 wt. %, and in some embodiments, from about 20 wt. % to about 40 wt. %. The film may also contain vinylpyrrolidone copolymers in an amount of from about 10 wt. % to about 40 wt. %, in some embodiments from about 15 wt. % to about 35 wt. %, and in some embodiments, from about 20 wt. % to about 30 wt. %, as well as polyquaternary ammonium polymers in an amount of from about 1 wt. % to about 30 wt. %, in some embodiments from about 5 wt. % to about 25 wt. %, and in some embodiments, from about 10 wt. % to about 20 wt. %. The film may also optionally contain cationic surfactants in an amount of from about 10 wt. % to about 50 wt. %, in some embodiments from about 15 wt. % to about 45 wt. %, and in some embodiments, from about 20 wt. % to about 40 wt. %. Regardless of its exact constituents, the present inventors have discovered that the resulting film is capable of exhibiting a residual degree of antiviral efficacy. The film is also physically stable so that it can still remain active after being abraded multiple times.

The present invention may be better understood with reference to the following examples.

Test Methods

Initial Virucidal Activity:
Initial virucidal activity was determined according to the ASTM E1052 Standard Test Method for Efficacy of Antimicrobial Agents Against Viruses in Suspension. Initial virucidal activity was determined against Feline calicivirus, ATCC VR-782 with a 10 minute exposure time. Results are reported as the mean $LOG_{10}$ reduction of Feline calicivirus (n=3).

Protocol for Propagation of Bacteriophage: Phi X174
1. Tryptic soy broth (TSB) containing 0.7% w/v agar (this mixture is called top agar) was prepared. Autoclave and store at 49° C. in a water bath or dry bead/sand bath.
2. Aliquot 4 ml of top agar into sterile 14 ml test tubes.
3. Inoculate 10 top agar tubes w/the concentrated phage stock from ATCC. Also add 100 μl of a 24 h *E. coli*

ATCC 13706 host culture that has been washed 1× in Butterfields Phosphate Buffer. (For frozen ATCC phage stock, add 500 µl TSB warmed to 49° C.)
4. Dump individual top agar tubes onto individual TSA plates warmed to room temperature. Ensure top agar is spread across the entire plate surface. Allow top agar to solidify, invert plates, and incubate for 24 hours @ 37° C.
5. Plates should show complete clearing (with the exception of possible pinpoint colonies throughout).
6. Add 2 mL of warm SM buffer (Teknova) to each plate and scrape the top agar with a sterile white Teflon policeman.
7. Using a serological pipette, transfer the scrapped top agar, liquid to a 15 ml conical centrifuge tube (1 tube per plate).
8. Vortex each tube for about 10-15 secs.
9. Centrifuge the tubes at 1000×g for 25 minutes. Make sure the tubes are distributed equally on each side of the centrifuge rotor.
10. After centrifuging, combine the resulting supernatant into a new sterile 50-mL centrifuge tube.
11. Wet the filter unit with sterile beef extract and replace the 50-mL centrifuge tube for collection of bacteriophage so it remains undiluted by the beef extract.
12. Pass all the collected bacteriophage supernatant through a 50-ml 0.2 um filtration unit.
13. Dilute and plate the filtrate to determine the PFU/ml. Store the filtrate in a refrigerator.

Residual Virucidal Activity:
I. Basic Reagents, Media, and Supplies
   1×1 inch non-frosted glass slides (carriers) free of visible damage and sterile.
   Sterile 100×15 mm petri dishes.
   Sterile, approximately 2" diameter 100% cotton swatches used to line sterile petri dishes.
   Bunsen burner, microbiological incinerator, or microtorch as appropriate.
   Micropipettes and appropriately sized sterile micropipette tips.
   Automatic pipettor (PipetAid or similar) and various sizes of sterile serological pipettes.
   Sterile 50 ml centrifuge tubes.
   Foam liners (FoamWiper, VWR Cat. #TW-TX 704) and sterile, approximately 2-inch-wide, strips of cotton cloth (TexWipe Clean Cotton Wipers, VWR Cat. #TW-TX 309).
   Gardco Washability and Wear Tester (Model D10V, Cat. #WA-2153, Paul N. Gardner Co., Inc., Pompano Beach, Fla.).
II. Reagents, Media, and Supplies for Microorganisms (Viruses)
   Pure stock preparation of each test system (bacteriophage).
   Pure stock of host bacteria for each test system.
   Sufficient quantity of 0.7% soft top agar tubes (TSA), tempered to 49±1° C.
   Sufficient quantity of vials containing the appropriate type and volume of neutralizer [e.g. 2× D/E broth].
   Sterile Butterfield's Phosphate Buffer
III. Procedure
   A. Preparation of Carriers
   Carriers (1"×1") glass) are cut from 1"×3" glass slides.
   Carriers are decontaminated by autoclave sterilization and then aseptically transferred to sterile Petri dishes lined with 1 piece of appropriately sized 100% cotton swatches.
   B. Preparation of Cultures Used in the Study
   A refrigerator stock of Phi X174 is diluted in sterile Butterfield's Phosphate Buffer to achieve a challenge inoculum of $10^8$ PFU/mL.
   A freezer stock of E. coli ATCC 13706 is propagated in Tryptic Soy Broth (TSB) for 24 hours at 37° C.
   C. Initial Carrier Inoculation
   Dilute refrigerator stock of Phi X174 in Butterfield's Phosphate Buffer to $1.0 \times 10^8$ PFU/mL to achieve $1.0 \times 10^6$ PFU per carrier
   0.010 mL of initial inoculation culture is spread gently to within ⅛ inch of the surface edge of each test and control carrier.
   All carriers are inoculated at room temp followed by immediate application of test product.
   D. Exposure of Control Carriers to Control Substance
   Control carriers are to remain untreated.
   Control carriers are placed in the biological safety cabinet overnight along with the test carriers.
   E. Exposure of Test Carriers to Test Substance
   Three test carriers (per test code) are treated by pipet application of 200 µl of the test substance.
   Carriers are placed in a biological safety cabinet and dried overnight.
   F. Abrasion and Re-Inoculation, and Final Carrier Inoculation
   All carriers undergo one abrasion cycle after overnight drying of the initial inoculation and test product application. The abrasions are performed using the Gardco Washability and Wear Tester (Model D10V, Cat. #WA-2153, Paul N. Gardner Co., Inc., Pompano Beach, Fla.). The weight of the fully assembled abrasion boat with the foam liner, cotton cloth, and clamps equaled 1084±3.0 g. The abrasion tester is set to a speed of 2.25 to 2.5. The abrasion cycle in this test equals 2 passes of the abrasion boat (e.g. left to right and then right to left). The foam liner and cotton cloths are replaced on the abrasion boat after each abrasion cycle, and the Gardner apparatus is decontaminated with 70% isopropanol and allowed to dry completely between set of abrasions to prevent carryover contamination. After the abrasion cycle, the carriers are re-inoculated with the final carrier inoculation. The final carrier inoculation must take place ≥24 hours after the initial inoculation. A refrigerator stock of Phi X174 is diluted in Butterfield's Phosphate Buffer to achieve a challenge inoculum of $1.0 \times 10^8$ PFU/mL. 0.010 mL of final inoculation culture is spread gently to within ⅛ inch of the surface edge of each test and control carrier for a contact time of 10 minutes.

| Days | Abrasion/Inoculation Procedure |
| --- | --- |
| Day 1 | Initial inoculation<br>Immediate application of test product/dry |
| Day 2 | One abrasion cycle is performed for each carrier<br>Final re-inoculation of test and control carriers<br>(≥24 hours after the initial inoculation) |

G. Efficacy Determination
   After the 10 minute contact time has elapsed, carriers are aseptically transferred to 50-mL centrifuge tubes containing 25 mL of neutralizer (2× D/E broth).
   Samples are vortexed for about 30 seconds.
   Control and test samples are serially diluted (1:10) in Butterfield's Phosphate Buffer through the $10^{-2}$ dilution.

Dilutions are plated in duplicate after adding 100 μL of the bacteriophage dilution with 100 μL of a washed overnight *E. coli* ATCC 13706 into 3 mL of TSA soft top agar. The top agar is vortexed and plated onto TSA plates. Plated dilutions should be $10^{-1}$, $10^{-2}$, and $10^{-3}$.

The TSA plates are incubated aerobically at 35±2° C. overnight.

Following incubation, the number of PFU (plaque forming units) is recorded.

Residual virucidal activity is determined by subtracting the mean $LOG_{10}$ PFU/mL recovered from test code from the mean $LOG_{10}$ PFU/mL recovered from the control code (n=3 for each code).

H. Inoculum Concentration Determinations

The titers of the bacteriophage inoculation and re-inoculation cultures are determined by performing 1:10 dilutions in Butterfield's Buffer.

Dilutions are plated in duplicate after adding 100 μL of the bacteriophage dilution with 100 μL of a washed overnight *E. coli* ATCC 13706 into 3 mL of TSA soft top agar. The top agar is vortexed and plated onto TSA plates. Plated dilutions should be $10^{-6}$, $10^{-7}$, and $10^{-8}$.

The TSA plates are incubated aerobically at 35±2° C. overnight.

Following incubation, the number of PFU (plaque forming units) is recorded.

I. Sterility Controls

Perform a streak for isolation on TSA of the *E. coli* ATCC 13706 used for plating.

Spread one tube of top agar onto a TSA plate to determine top agar sterility.

Example 1

A disinfectant composition was formed that contained 94.6 wt. % water, 1.25 wt. % of benzethonium chloride, 1.25 wt. % citric acid, 1.9 wt. % of Copolymer 958, 1.0 wt. % of Mirapol™ A 15. Copolymer 958 includes 50% vinylpyrrolidone/dimethylaminoethylacylrate in ethanol. Mirapol™ A 15 includes 60-70% Polyquaternium-2 in water. The final pH level was 2.76.

Example 2

A disinfectant composition was formed that contained 94.35 wt. % water, 1.25 wt. % of benzethonium chloride, 1.5 wt. % maleic acid, 1.9 wt. % of Copolymer 958, 1.0 wt. % of Mirapol™ A 15. The final pH level was 1.42.

Example 3

A disinfectant composition was formed as described in Example 2 except that the final pH was adjusted with sodium hydroxide to a level of 2.00.

Example 4

A disinfectant composition was formed as described in Example 2 except that the final pH was adjusted with sodium hydroxide to a level of 2.52.

Example 5

A disinfectant composition was formed as described in Example 2 except that the final pH was adjusted with sodium hydroxide to a level of 3.03.

Example 6

A disinfectant composition was formed that contained 94.35 wt. % water, 1.25 wt. % of benzethonium chloride, 1.5 wt. % malic acid, 1.9 wt. % of Copolymer 958, 1.0 wt. % of Mirapol™ A 15. The final pH level was 2.37.

Example 7

A disinfectant composition was formed as described in Example 6, except that the final pH was adjusted with sodium hydroxide to a level of 2.49.

Example 8

A disinfectant composition was formed as described in Example 6, except that the final pH was adjusted with sodium hydroxide to a level of 2.99.

Example 9

A disinfectant composition was formed that contained 93.7 wt. % water, 1.25 wt. % of benzethonium chloride, 2.15 wt. % sulfosuccinic acid, 1.9 wt. % of Copolymer 958, 1.0 wt. % of Mirapol™ A 15. The final pH level was 1.18.

Example 10

A disinfectant composition was formed as described in Example 9, except that the final pH was adjusted with sodium hydroxide to a level of 2.00.

Example 11

A disinfectant composition was formed as described in Example 9, except that the final pH was adjusted with sodium hydroxide to a level of 2.48.

Example 12

A disinfectant composition was formed as described in Example 9, except that the final pH was adjusted with sodium hydroxide to a level of 3.01.

Example 13

A disinfectant composition was formed that contained 94.35 wt. % water, 1.25 wt. % of benzethonium chloride, 1.50 wt. % phosphoric acid, 1.9 wt. % of Copolymer 958, 1.0 wt. % of Mirapol™ A 15. The final pH level was 1.51.

Example 14

A disinfectant composition was formed as described in Example 13, except that the final pH was adjusted with sodium hydroxide to a level of 1.99.

Example 15

A disinfectant composition was formed as described in Example 13, except that the final pH was adjusted with sodium hydroxide to a level of 2.48.

Example 16

A disinfectant composition was formed as described in Example 13, except that the final pH was adjusted with sodium hydroxide to a level of 3.00.

Example 17

A disinfectant composition was formed that contained 92.85 wt. % water, 1.25 wt. % of benzethonium chloride, 3.00 wt. % glyoxylic acid, 1.9 wt. % of Copolymer 958, 1.0 wt. % of Mirapol™ A 15. The final pH level was 2.02.

Example 18

A disinfectant composition was formed as described in Example 17, except that the final pH was adjusted with sodium hydroxide to a level of 2.49.

Example 19

A disinfectant composition was formed as described in Example 17, except that the final pH was adjusted with sodium hydroxide to a level of 2.99.

Example 20

A disinfectant composition was formed that contained 91.85 wt. % water, 1.25 wt. % of benzethonium chloride, 4.00 wt. % malic acid, 1.9 wt. % of Copolymer 958, 1.0 wt. % of Mirapol™ A 15. The final pH level was 2.12.

Example 21

A disinfectant composition was formed that contained 92.44 wt. % water, 1.25 wt. % of benzethonium chloride, 3.41 wt. % maleic acid, 1.9 wt. % of Copolymer 958, 1.0 wt. % of Mirapol™ A 15. The final pH was adjusted with sodium hydroxide to a level of 2.1.

Results

Once formed, the initial virucidal activity of Examples 1-19 was tested according to the method described above. The results are set forth in the table below.

| Example | Acid | pH Level | $LOG_{10}$ Reduction |
|---|---|---|---|
| 1 | Citric | 2.76 | 3.96 |
| 2 | Maleic | 1.42 | ≥4.00 |
| 3 | | 2.00 | ≥4.00 |
| 4 | | 2.52 | ≥4.00 |
| 5 | | 3.03 | 3.25 |
| 6 | Malic | 2.37 | 0.75 |
| 7 | | 2.49 | 1.58 |
| 8 | | 2.99 | 1.91 |
| 9 | Sulfosuccinic | 1.18 | ≥3.83 |
| 10 | | 2.00 | 2.25 |
| 11 | | 2.48 | ≥2.75 |
| 12 | | 3.01 | 1.91 |
| 13 | Phosphoric | 1.51 | ≥3.83 |
| 14 | | 1.99 | 2.83 |
| 15 | | 2.48 | 3.08 |
| 16 | | 3.00 | 2.91 |
| 17 | Glyoxylic | 2.02 | 3.58 |
| 18 | | 2.49 | ≥3.75 |
| 19 | | 2.99 | 2.92 |

Residual virucidal activity tests were also performed for Examples 1, 2, 6, 9, 13, 20 and 21. The results are set forth in the table below.

| Example | Acid | pH Level | $LOG_{10}$ Reduction |
|---|---|---|---|
| 1 | Citric | 2.76 | 0.6 |
| 2 | Maleic | 1.42 | 3.4 |
| 6 | Malic | 2.37 | 0.9 |
| 9 | Sulfosuccinic | 1.18 | ≥3.5 |
| 13 | Phosphoric | 1.51 | ≥3.5 |
| 20 | Malic | 2.12 | 1.8 |
| 21 | Maleic | 2.1 | ≥3.5 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A disinfectant composition comprising:
   i) an acid;
   ii) a vinylpyrrolidone copolymer having the following general formula:

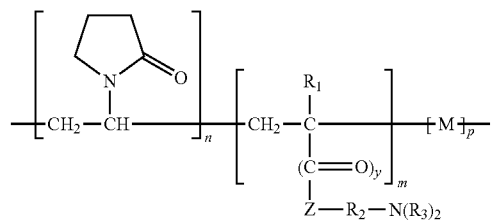

wherein,
   n is from 20 to 99;
   m is from 1 to 80;
   p is from 0 to 50, and wherein the total of n+m+p is 100;
   $R_1$ is H or a $C_1$ to $C_4$ alkyl;
   Z is O, S, or NH;
   $R_2$ is $(CH_2)_x$;
   x is from 1 to 18;
   y is 0 or 1;
   $R_3$ is independently hydrogen or a $C_1$ to $C_4$ alkyl; and
   M is a vinyl or vinylidene monomer copolymerizable with vinyl pyrrolidone;
   iii) a polyquaternary ammonium polymer having the following general structure:

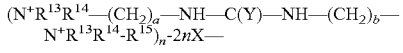

wherein,
   $R^{13}$ and $R^{14}$ are independently alkyl, hydroxyalkyl, or $-CH_2CH_2(OCH_2CH_2)_cOH$;
   $R^{15}$ is a linking group and may be $(CH_2)_d$ or $\{(CH_2)_e O(CH_2)_f\}_g$;
   Y is O, S or NH;
   a, b, c, d, e and f are each independently from 1 to 6;
   g is from 1 to 4;
   n is at least 2; and
   $X^-$ is an anion; and
   iv) a cationic surfactant;
wherein the composition has a pH of about 1 to about 3.5, and further wherein the vinylpyrrolidone copolymer is present in an amount from about 50 to about 90 parts per 100 parts of acids employed in the composition, and wherein the polyquaternary ammonium polymer is present in an amount from about 30 to about 70 parts per 100 parts of acids employed in the composition; and wherein the composition contains a solvent system that includes one or more solvents, wherein the solvent system constitutes from about 80 wt. % to about 99.9 wt. % of the composition, wherein water constitutes at least about 90 wt. % of the solvent system.

2. The disinfectant composition of claim 1, wherein acids constitute from about 0.1 wt. % to about 10 wt. % of the composition.

3. The disinfectant composition of claim 1, wherein the vinylpyrrolidone copolymer constitutes from about 0.2 wt. % to about 5 wt. % of the composition.

4. The disinfectant composition of claim 1, wherein the polyquaternary ammonium polymer constitutes from about 0.1 wt. % to about 3 wt. % of the composition.

5. The disinfectant composition of claim 1, wherein the weight ratio of the vinylpyrrolidone copolymer to the polyquaternary ammonium polymer is from about 1.0 to about 8.0.

6. The disinfectant composition of claim 1, wherein the acid is an inorganic acid.

7. The disinfectant composition of claim 1, wherein the acid is an organic carboxylic acid.

8. The disinfectant composition of claim 7, wherein the organic carboxylic acid is citric acid, malic acid, maleic acid, mandelic acid, succinic acid, sulfosuccinic acid, tannic acid, lactic acid, glyoxylic acid, gallic acid, fumaric acid, tartaric acid, formic acid, benzoic acid, 4-aminobenzoic acid, 4-bromo-DL-mandelic acid, or a combination thereof.

9. The disinfectant composition of claim 1, wherein the acid has a first acid dissociation constant of about 5.0 or less.

10. The disinfectant composition of claim 1, wherein the vinylpyrrolidone copolymer has the following general structure:

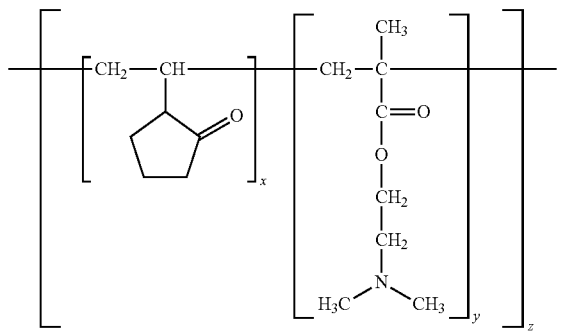

wherein x, y and z are at least 1.

11. The disinfectant composition of claim 1, wherein the polyquaternary ammonium polymer has the following general structure:

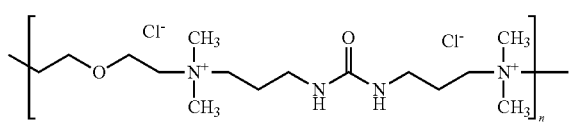

wherein n is as at least 2.

12. The disinfectant composition of claim 1, wherein the cationic surfactant is a benzalkonium halide having an alkyl chain length of $C_{12}$-$C_{16}$, a benzalkonium halide substituted with alkyl groups on the phenyl ring, a dimethyldialkylammonium halide in which the alkyl groups have chain lengths of $C_8$-$C_{18}$, a benzethonium halide, an alkyl substituted benzethonium halide, or a combination thereof.

13. The disinfectant composition of claim 1, wherein the composition exhibits a $\log_{10}$ reduction of about 1.5 or more after being exposed to a non-enveloped virus for 10 minutes.

14. The disinfectant composition of claim 13, wherein the non-enveloped virus includes rhinovirus, poliovirus, enterovirus, coxsackievirus, adenovirus, norovirus, papillomavirus, feline calicivirus, hepatitis A virus, parvovirus, rotavirus, or a combination thereof.

15. The disinfectant composition of claim 1, wherein the composition exhibits a $\log_{10}$ reduction of about 1.5 or more after being exposed to Feline calicivirus (ATCC VR-782) for 10 minutes.

16. A method for disinfecting a surface, the method comprising contacting the surface with the disinfectant composition of claim 1.

17. The method of claim 16, wherein the surface is a hard surface.

18. The method of claim 16, wherein the disinfectant composition is disposed on a wipe prior to being applied to the surface.

19. The method of claim 16, wherein the composition forms a film on the surface after being applied thereto.

20. A film that is capable of exhibiting residual antiviral activity, wherein the film is formed according to the following process:

applying the disinfectant composition according to claim 1 to a surface, and evaporating at least a portion of the solvent system.

21. The film of claim 20, wherein the weight ratio of the vinylpyrrolidone copolymer to the polyquaternary ammonium polymer is from about 1.0 to about 8.0.

22. The film of claim 20, wherein the acid has a first acid dissociation constant of from about 1.0 to about 5.0.

23. The film of claim 20, wherein the vinylpyrrolidone copolymer has the following general structure:

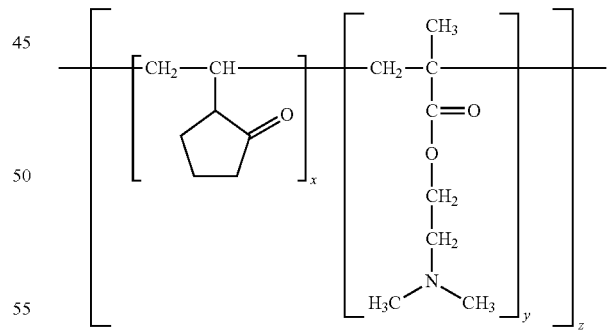

wherein x, y and z are at least 1.

24. The film of claim 20, wherein the polyquaternary ammonium polymer has the following general structure:

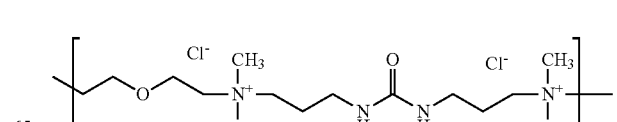

wherein n is as at least 2.

25. The film of claim 20, wherein the acid constitutes from about 10 wt. % to about 50 wt. % of the film, the vinylpyrrolidone copolymer constitute from about 10 wt. % to about 40 wt. % of the film, and the polyquaternary ammonium polymer constitutes from about 1 wt. % to about 30 wt. % of the film.

26. The film of claim 20, wherein the film exhibits a $\log_{10}$ reduction of about 0.5 or more after being exposed to a non-enveloped virus for 10 minutes.

27. The film of claim 26, wherein the non-enveloped virus includes rhinovirus, poliovirus, enterovirus, coxsackievirus, adenovirus, norovirus, papillomavirus, feline calicivirus, hepatitis A virus, parvovirus, rotavirus, or a combination thereof.

28. The film of claim 26, wherein the film exhibits the log reduction after application to a surface for 24 hours.

29. The film of claim 26, wherein the film exhibits the log reduction after application to a surface for 48 hours.

\* \* \* \* \*

UNITED STATES PATENT AND TRADEMARK OFFICE
CERTIFICATE OF CORRECTION

| | | |
|---|---|---|
| PATENT NO. | : 10,874,100 B2 | Page 1 of 1 |
| APPLICATION NO. | : 15/744091 | |
| DATED | : December 29, 2020 | |
| INVENTOR(S) | : Amy L. Vanden Heuvel et al. | |

It is certified that error appears in the above-identified patent and that said Letters Patent is hereby corrected as shown below:

On the Title Page

Item (72) Inventors:

"Douglas R. Hoffman, Neeneha, WI (US)" should be "Douglas R. Hoffman, Neenah, WI (US)"

"Corey T. Cunnington" should be "Corey T. Cunningham"

Signed and Sealed this
Thirteenth Day of December, 2022

Katherine Kelly Vidal
*Director of the United States Patent and Trademark Office*